United States Patent [19]
Galt et al.

[11] 3,979,513
[45] Sept. 7, 1976

[54] 1'-SUBSTITUTED-9,10-DIHYDROANTHRACENE-9-SPIRO-4'-PIPERIDINE DERIVATIVES

[75] Inventors: Ronald Hilson Begg Galt; Alasdair Thomas Glen, both of Macclesfield, England

[73] Assignee: Imperial Chemical Industries Limited, London, England

[22] Filed: Jan. 16, 1975

[21] Appl. No.: 541,693

[30] Foreign Application Priority Data

Feb. 4, 1974 United Kingdom............... 5018/74

[52] U.S. Cl............................. 424/267; 260/293.62; 260/351; 260/513 R; 260/618 F
[51] Int. Cl.²....................................... C07D 221/20
[58] Field of Search................ 260/293.62; 424/267

[56] References Cited
UNITED STATES PATENTS

| | | | |
|---|---|---|---|
| 3,014,911 | 12/1961 | Engelhardt...................... | 260/293.62 |
| 3,048,595 | 8/1962 | Zirkle ............................ | 260/293.58 |
| 3,418,324 | 12/1968 | Rice et al....................... | 260/293.62 |
| 3,652,558 | 3/1972 | Lunsford et al. .............. | 260/293.62 |
| 3,654,287 | 4/1972 | Dykstra.......................... | 260/293.62 |

*Primary Examiner*—Natalie Trousof
*Attorney, Agent, or Firm*—Cushman, Darby & Cushman

[57] ABSTRACT

The disclosure relates to dihydroanthracene derivatives which possess analgesic activity, to processes for their manufacture and to compositions containing them. Typical of the dihydroanthracene derivatives disclosed is 6-chloro-4-hydroxy-1'-methyl-9,10-dihydroanthracene-9-spiro-4'-piperidine.

10 Claims, No Drawings

1'-SUBSTITUTED-9,10-DIHYDROANTHRACENE-9-SPIRO-4'-PIPERIDINE DERIVATIVES

This invention relates to dihydroanthracene derivatives which possess analgesic properties.

According to the invention there is provided a dihydroanthracene derivative of the formula:

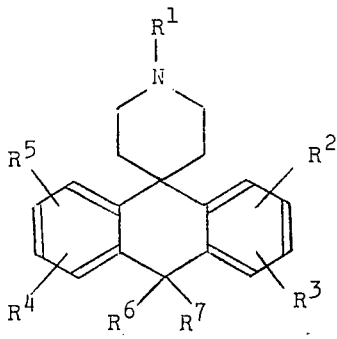

wherein R¹ stands for
1. a hydrogen atom; or
2. an alkyl radical of 1 to 10 carbon atoms;
3. an alkenyl radical of 3 to 8 carbon atoms;
4. A cycloalkylalkyl radical of 4 to 7 carbon atoms, optionally substituted in the cycloalkyl nucleus by an aryl radical of 6 to 10 carbon atoms or by one or two alkyl radicals of 1 to 3 carbon atoms;
5. an arylalkyl radical of 4 to 10 carbon atoms optionally substituted in the aryl nucleus by one to three halogen atoms or alkyl radicals of 1 to 3 carbon atoms;
6. a hydroxyalkyl radical of 2 to 5 carbon atoms; or
7. a dialkylaminoalkyl radical of 4 to 8 carbon atoms;

R², R³, R⁴ and R⁵, which may be the same or different, stand for
8. hydrogen atoms; or
9. halogen atoms; or
10. alkyl radicals of 1 to 5 carbon atoms;
11. haloalkyl radicals of 1 to 5 carbon atoms;
12. alkoxy radicals of 1 to 5 carbon atoms;
13. hydroxy radicals;
14. alkanoyloxy radicals of 1 to 5 carbon atoms;
15. aroyloxy radicals of 7 to 10 carbon atoms, optionally substituted in the aryl nucleus by one to three halogen atoms or alkyl radicals of 1 to 3 carbon atoms; or
16. hydroxyalkyl radicals of 1 to 5 carbon atoms;

R⁶ stands for
17. a hydrogen atom; or
18. an alkyl radical of 1 to 3 carbon atoms;
19. an alkylthio radical of 1 to 3 carbon atoms;
20. an alkanoyloxy radical of 1 to 3 carbon atoms; or
21. a hydroxy radical; and R⁷ stands for
22. a hydrogen atom; or
23. an alkyl radical of 1 to 3 carbon atoms;

or R⁶ and R⁷ together stand for
24. an oxygen atom; or
25. a methylene radical; and the pharmaceutically-acceptable acid-addition salts thereof.

It is to be understood that when R¹ is an alkenyl, hydroxyalkyl or dialkylaminoalkyl radical, the double bond, oxygen atom or nitrogen atom it contains is separated from the nitrogen atom of the spiropiperidine ring by at least one carbon atom, at least two carbon atoms or at least two carbon atoms respectively.

The numbering system used in this specification to describe the position of a substituent on the dihydroanthracene nucleus is as follows:

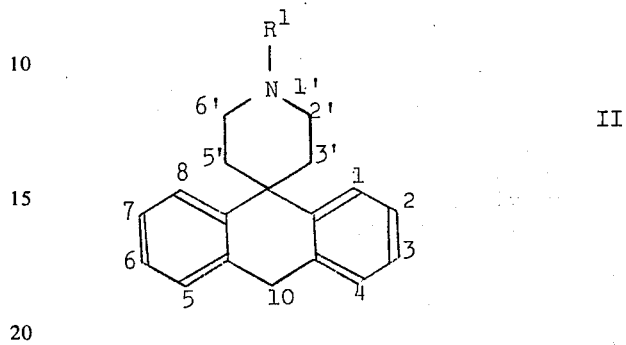

Reference to substitution at a particular position means substitution at that numbered position in the dihydroanthracene nucleus as defined immediately above.

A particular value for R¹ when it is an alkyl radical is such a radical of 1 to 5 carbon atoms, for example a methyl, ethyl, n-propyl or i-propyl radical.

A particular value for R¹ when it is an alkenyl radical is such a radical of 3 to 5 carbon atoms, for example an allyl radical.

A particular value for R¹ when it is a cycloalkylalkyl, arylalkyl, hydroxyalkyl or dialkylaminoalkyl radical is a cyclopropylmethyl, phenethyl, furfuryl, 2-hydroxyethyl or 2-dimethylaminoethyl radical.

A particular value for R², R³, R⁴ or R⁵ when it is an alkyl, haloalkyl, alkoxy or alkanoyloxy radical is such a radical of 1 to 3 carbon atoms, for example a methyl, trifluoromethyl, methoxy or acetoxy radical.

A particular value for R², R³, R⁴ or R⁵ when it is a halogen atom or an aroyloxy radical is a chlorine atom or a benzoyloxy radical.

A particular value for R⁶ when it is an alkyl, alkylthio or alkanoyloxy radical is a methyl, ethylthio or acetoxy radical.

A particular value for R⁷ when it is an alkyl radical is a methyl radical.

Particular groups of compounds of the invention, each substituent being described by number as defined above, are as follows:

Those wherein R¹ is as defined above, R², R³, R⁴ and R⁵ stand for values 8, 9, 10, 11, 12, 13, 14 or 15, for example hydrogen or chlorine atoms or methyl, trifluoromethyl, methoxy, hydroxy, acetoxy or benzoyloxy radicals, provided that when R² and R³ are both other than hydrogen atoms they are the same and when R⁴ and R⁵ are both other than hydrogen atoms they are the same, R⁶ stands for value 17, 18 or 21, for example a hydrogen atom or a methyl or hydroxy radical, and R⁷ stands for value 22 or 23, for example a hydrogen atom or a methyl radical.

Further particular groups of compounds of the invention are as follows:
R¹ = 1 or 2
R² = 12, 13, 14 or 15 substituted at the 4-position
R³, R⁴, R⁵ = 8
R⁶ = 17, 18 or 21

$R^7 = 22$ or 23 or $R^6, R^7 = 25$
$R^1 = 1$ or 2
$R^2 = 12, 13, 14$ or 15 substituted at the 4-position
$R^3, R^4, R^5 = 8$
$R^6 = 17, 18$ or 21
$R^7 = 22$ or 23
$R^1 = $ hydrogen or methyl
$R^2 = 12, 13, 14$ or 15 substituted at the 4-position
$R^3, R^4, R^5 = 8$
$R^6 = $ hydrogen, methyl or hydroxy
$R^7 = $ hydrogen or methyl or $R^6, R^7 = 25$
$R^1 = $ hydrogen or methyl
$R^2 = 12, 13, 14$ or 15 substituted at the 4-position
$R^3, R^4, R^5 = 8$
$R^6 = $ hydrogen or hydroxy
$R^7 = $ hydrogen or methyl
$R^1 = $ hydrogen or methyl
$R^2 = $ methoxy, hydroxy, acetoxy or benzoyloxy substituted at the 4-position
$R^3, R^4, R^5 = 8$
$R^6 = $ hydrogen, methyl or hydroxy
$R^7 = $ hydrogen or methyl or $R^6, R^7 = 25$
$R^1 = $ hydrogen or methyl
$R^2 = $ methoxy, hydroxy, acetoxy or benzoyloxy substituted at the 4-position
$R^3, R^4, R^5 = 8$
$R^6 = $ hydrogen or hydroxy
$R^7 = $ hydrogen or methyl
$R^1 = $ hydrogen or methyl
$R^2 = $ methoxy, hydroxy, or acetoxy substituted at the 4-position
$R^3, R^4, R^5 = 8$
$R^6 = $ hydroxy
$R^7 = $ methyl or $R^6, R^7 = $ hydrogen
$R^1 = 1, 2, 3, 4, 5, 6$ or 7
$R^2 = 8, 9, 10, 11, 12$ or 16 substituted at the 2- or 3-position
$R^3, R^4, R^5 = 8$
$R^6 = $ hydrogen, hydroxy or acetoxy
$R^7 = $ hydrogen or methyl or $R^6, R^7 = 25$
$R^1 = 1, 2, 3, 4, 5, 6$ or 7
$R^2 = 8, 9, 10, 11, 12$ or 16 substituted at the 2- or 3-position
$R^3, R^4, R^5 = 8$
$R^6 = $ hydrogen or hydroxy
$R^7 = $ hydrogen or methyl
$R^1 = 2$
$R^2 = 8$, or 10 substituted at the 2-position
$R^3, R^4, R^5 = 8$
$R^6 = $ hydrogen, hydroxy or acetoxy
$R^7 = $ hydrogen or methyl or $R^6, R^7 = 25$
$R^1 = 2$
$R^2 = 8$, or 10 substituted at the 2-position
$R^3, R^4, R^5 = 8$
$R^6 = $ hydrogen or hydroxy
$R^7 = $ hydrogen or methyl
$R^1 = $ methyl
$R^2 = $ H, or methyl substituted at the 2-position
$R^3, R^4, R^5 = 8$
$R^6 = 21$
$R^7 = $ hydrogen or methyl
$R^1$ 32 1, 2, 3, 4, 5, 6 or 7
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = 17, 20$ or 21
$R^7 = 22$ or 23 or $R^6, R^7 = 24$
$R^1 = 1, 2, 3, 4, 5, 6$ or 7
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = 17$ or 21
$R^7 = 22$ or 23 or $R^6, R^7 = 24$
$R^1 = 2$
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = 17, 20$ or 21
$R^7 = 22$ or 23 or $R^6, R^7 = 24$
$R^1 = 2$
$R^2 = 12, 13, 14$ or 15 substituted at the 4-position
$R^4 = 9, 10, 11, 12, 13$ or 14 substituted at the 5-, 6- or 7-position
$R^3, R^5 = 8$
$R^6 = 17$ or 21
$R^7 = 22$ or 23 or $R^6, R^7 = 24$
$R^1 = 1, 2, 3, 4, 5, 6$ or 7
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = $ hydrogen, hydroxy or acetoxy
$R^7 = $ hydrogen or methyl
$R^1 = 2$
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = $ hydrogen, hydroxy or acetoxy
$R^7 = $ hydrogen or methyl
$R^1 = 1, 2, 3, 4, 5, 6$ or 7
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = 17$ or 21
$R^7 = $ hydrogen or methyl
$R^1 = 2$
$R^2 = 12, 13, 14$ or 15 substituted at the 4-position
$R^4 = 9, 10, 11, 12, 13$ or 14 substituted at the 5-, 6-, 7- or 8-position
$R^3, R^5 = 8$
$R^6 = 17$ or 21
$R^7 = $ hydrogen or methyl
$R^1 = $ methyl
$R^2 = $ methoxy, hydroxy or acetoxy substituted at the 4-position
$R^4 = $ chlorine, methyl, trifluoromethyl, methoxy, hydroxy or acetoxy substituted at the 5-, 6-, 7- or 8-position
$R^3, R^5 = 8$
$R^6 = 17$ or 21
$R^7 = $ hydrogen or methyl
$R^1 = $ methyl
$R^2 = $ methoxy, hydroxy or acetoxy substituted at the 4-position
$R^4 = $ chlorine or trifluoromethyl substituted at the 5-, 6-, 7- or 8-position, or hydroxy or methoxy substituted at the 5-position
$R^3, R^5 = 8$
$R^6, R^7 = $ hydrogen Particular compounds of the invention are described in the Examples and of these preferred compounds are:

that wherein
$R^1$ = methyl
$R^2$ = hydroxy substituted at the 4-position
$R^3$, $R^4$, $R^5$ = hydrogen
$R^6$ = hydroxy
$R^7$ = methyl
and that wherein
$R^1$ = methyl
$R^2$ = hydroxy substituted at the 4-position
$R^4$ = chlorine substituted at the 6-position
$R^3$, $R^5$, $R^6$, $R^7$ = hydrogen A suitable pharmaceutically-acceptable acid-addition salt of the invention is, for example, a hydrochloride, hydrobromide, phosphate or sulphate, or a citrate, acetate, maleate or oxalate.

The dihydroanthracene derivative of the invention may be manufactured by methods known in themselves for the manufacture of chemically analogous compounds, $R^1$, $R^2$, $R^3$, $R^4$, $R^5$, $R^6$ and $R^7$ having the meanings stated above, for example:

a. for those compounds in which $R^1$ has a value other than that numbered 1, $R^2$, $R^3$, $R^4$ and $R^5$ have values other than those numbered 13, 14 or 15 and $R^6$ and $R^7$ have values other than that numbered 25, reacting a compound of the formula III:

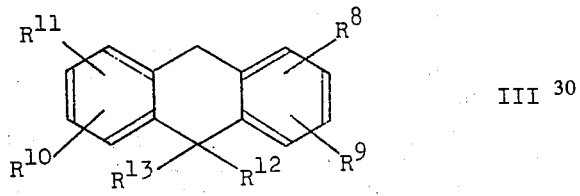

III wherein $R^8$, $R^9$, $R^{10}$ and $R^{11}$ have the values stated above for $R^2$, $R^3$, $R^4$ and $R^5$ other than those numbered 13, 14 or 15 and $R^{12}$ and $R^{13}$ have the values stated above for $R^6$ and $R^7$ other than that numbered 25, with a compound of the formula $R^{14}N(CH_2CH_2X)_2$ wherein $R^{14}$ has the value stated above for $R^1$ other than that numbered 1 and X is a displaceable radical. X may be, for example, a displaceable halogen atom, for example a chlorine or bromine atom, or an arene- or alkanesulphonyloxy radical, for example a toluene-p-sulphonyloxy or methanesulphonyloxy radical. The reaction is preferably conducted in the presence of a base, for example sodium methylsulphinylmethide, in a diluent or solvent, for example dimethyl sulphoxide, and is preferably conducted under an inert atmosphere.

b. for those compounds in which $R^2$, $R^3$, $R^4$ and $R^5$ have values other than those numbered 11, 14 or 15 and $R^6$ and $R^7$ have values other than those numbered 20 or 24, reducing a compound of the formula IV:

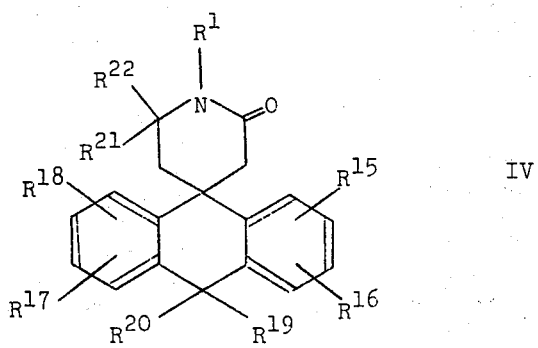

IV wherein $R^{15}$, $R^{16}$, $R^{17}$ and $R^{18}$ have the values stated above for $R^2$, $R^3$, $R^4$ and $R^5$ other than those numbered 11, 14 or 15, $R^{19}$ and $R^{20}$ have the values stated above for $R^6$ and $R^7$ other than those numbered 20 or 24 and $R^{21}$ and $R^{22}$ stand for hydrogen atoms or together stand for an oxygen atom. The reduction may be carried out with a complex metal hydride, for example lithium aluminium hydride, in a diluent or solvent, for example diethyl ether or tetrahydrofuran, and may be accelerated or completed by the application of heat, for example by heating to the boiling point of the diluent or solvent.

c. for those compounds in which $R^2$, $R^3$, $R^4$ and $R^5$ have values other than that numbered 13 substituted at the 2-, 4-, 5- or 7-position, $R^6$ is a hydroxy radical and $R^7$ is a hydrogen atom, reducing a compound of the formula V:

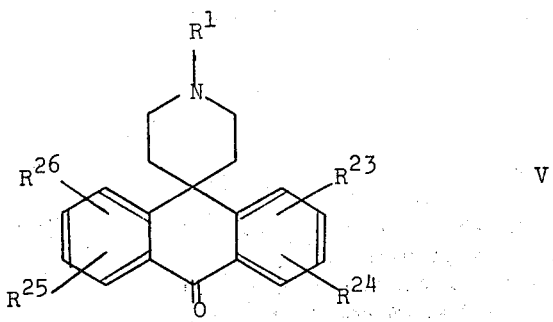

V wherein $R^{23}$, $R^{24}$, $R^{25}$ and $R^{26}$ have the values stated above for $R^2$, $R^3$, $R^4$ and $R^5$ other than that numbered 13 substituted at the 2-, 4-, 5- or 7-position. The reduction may be carried out with a borohydride, for example sodium borohydride, in a diluent or solvent such as ethanol. Alternatively the reduction may be carried out with a complex metal hydride under the same conditions as for process (b).

d. for those compounds in which $R^2$, $R^3$, $R^4$ and $R^5$ have values other than those numbered 14 or 15 and $R^6$ has a value other than that numbered 20, reaction of a compound of the formula VI:

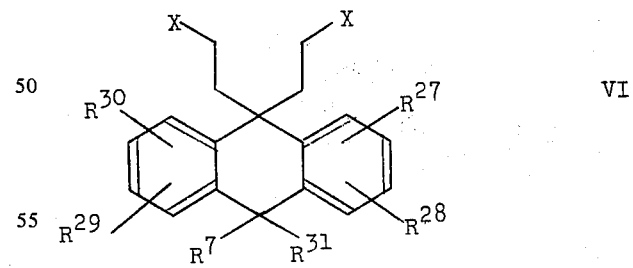

VI wherein $R^{27}$, $R^{28}$, $R^{29}$ and $R^{30}$ have the values stated above for $R^2$, $R^3$, $R^4$ and $R^5$ other than those numbered 14 or 15, $R^{31}$ has the value stated above for $R^6$ other than that numbered 20 and X is as above, with a compound of the formula $R^1$-$NH_2$. The reaction may be conducted by heating the reactants in a diluent or solvent, for example ethanol, n-propanol or xylene. Where a temperature higher than the boiling point of the diluent or solvent is required, the reaction may be conducted in a pressure vessel. Alternatively where the boiling point of the reactant of the formula $R^1$-$NH_2$ is sufficiently high, no diluent or solvent may be required.

e. for those compounds in which $R^2$, $R^3$, $R^4$ and $R^5$ have values other than that numbered 9 and $R^6$ and $R^7$ are both hydrogen atoms, reduction of a compound of the formula VII:

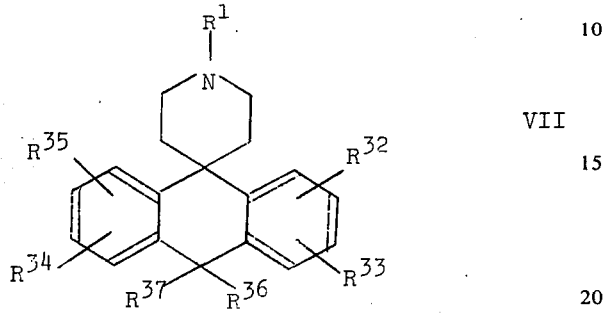

VII wherein $R^{32}$, $R^{33}$, $R^{34}$ and $R^{35}$ have the values stated above for $R^2$, $R^3$, $R^4$ and $R^5$ other than that numbered 9 and $R^{36}$ and $R^{37}$ together stand for an oxygen atom or $R^{36}$ is a hydroxyl radical and $R^{37}$ is a hydrogen atom. The reduction may be carried out by heating with aluminium isopropoxide, for example at 220°C. Alternatively, when at least one of $R^{32}$, $R^{33}$, $R^{34}$ or $R^{35}$ is a hydroxy radical substituted at the 2-, 4-, 5-, or 7-position, the reduction may be accomplished with lithium aluminium hydride or sodium borohydride in a diluent or solvent, for example diethyl ether or ethanol respectively.

f. for those compounds in which $R^1$ has a value other than that numbered 1 or 6, $R^2$, $R^3$, $R^4$ and $R^5$ have values other than that numbered 16 and $R^6$ and $R^7$ together stand for an oxygen atom, oxidation of a compound of the formula VIII:

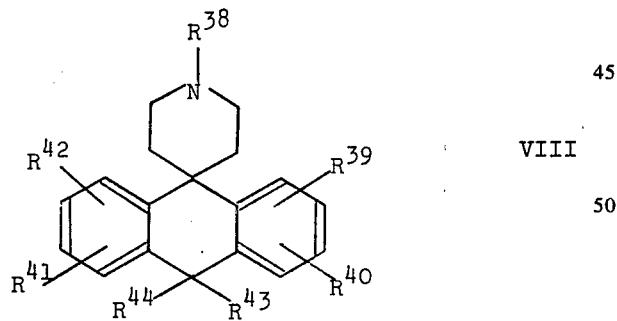

VIII wherein $R^{38}$ has the value stated above for $R^1$ other than that numbered 1 or 6, $R^{39}$, $R^{40}$, $R^{41}$ and $R^{42}$ have the values stated above for $R^2$, $R^3$, $R^4$ and $R^5$ other than that numbered 16, $R^{43}$ stands for a hydrogen atom or a hydroxy radical and $R^{44}$ stands for a hydrogen atom. The oxidising agent may be, for example, sodium dichromate in sulphuric acid or chromium trioxide in acetic acid.

g. for those compounds in which $R^2$, $R^3$, $R^4$ and $R^5$ have values other than those numbered 9, 14 or 15, $R^6$ is a hydroxy radical and $R^7$ is an alkyl radical, reaction of a compound of the formula IX:

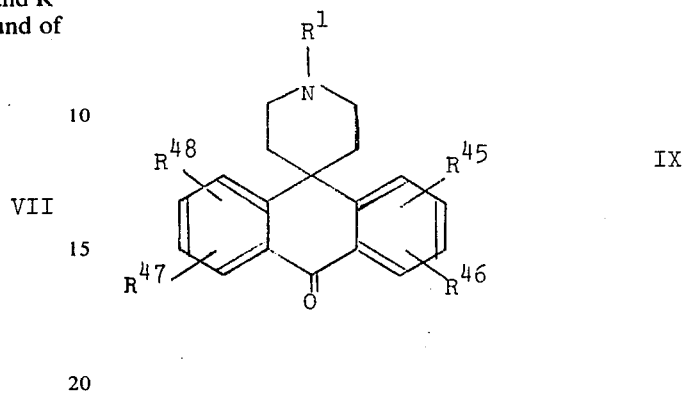

IX wherein $R^{45}$, $R^{46}$, $R^{47}$ and $R^{48}$ have the values stated above for $R^2$, $R^3$, $R^4$ and $R^5$ other than those numbered 9, 14 or 15 with a Grignard reagent of the formula $R^{49}MgY$ or a metal alkyl of the formula metal-$R^{49}$ wherein $R^{49}$ is an alkyl radical and Y is a chlorine, bromine or iodine atom. The reaction may be carried out in a diluent or solvent such as diethyl ether or tetrahydrofuran.

h. for those compounds in which at least one of $R^2$, $R^3$, $R^4$ and $R^5$ is a hydroxy radical and the remaining members of $R^2$, $R^3$, $R^4$ and $R^5$ have values other than those numbered 14 or 15 and $R^6$ has a value other than that numbered 20, replacement by hydrogen of the alkyl part of the alkoxy radical in a compound of the formula X:

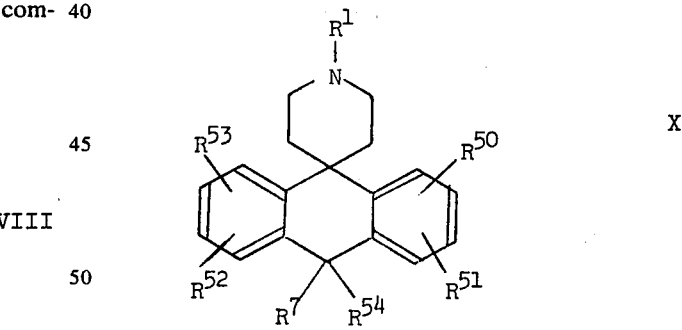

X wherein at least one of $R^{50}$, $R^{51}$, $R^{52}$ and $R^{53}$ is an alkoxy radical and the remaining members of $R^{50}$, $R^{51}$, $R^{52}$ and $R^{53}$ have the values stated above for $R^2$, $R^3$, $R^4$ and $R^5$ other than those numbered 14 or 15 and $R^{54}$ has the value stated in claim 1 for $R^6$ other than that numbered 20. The reaction may be carried out with pyridine hydrochloride, for example by heating at 200°C.; with boron tribromide, in a solvent such as methylene chloride, at or below 0°C.; with HBr in acetic acid at reflux or with 48% w/v aqueous HBr at reflux; or with sodium ethanethiolate or sodium thiophenoxide, for example by heating in a solvent such as dimethyl formamide at 100°–150°C.

i. for those compounds in which $R^1$ has a value other than that numbered 6, at least one of $R^2$, $R^3$, $R^4$, $R^5$ and $R^6$ has a value numbered 14, 15 or 20 and the remaining members of $R^2$, $R^3$, $R^4$, $R^5$ and $R^6$ have values other than those numbered 16 or 21, reaction of a compound of the formula XI:

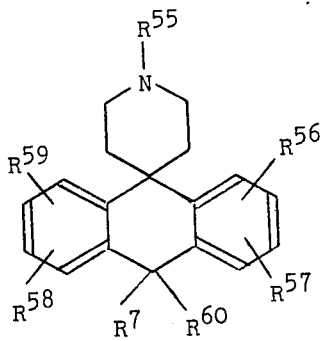

XI wherein $R^{55}$ has the value stated above for $R^1$ other than that numbered 6, at least one of $R^{56}$, $R^{57}$, $R^{58}$, $R^{59}$ and $R^{60}$ is a hydroxy radical and the remaining members of $R^{56}$, $R^{57}$, $R^{58}$, $R^{59}$ and $R^{60}$ have the values stated above for $R^2$, $R^3$, $R^4$, $R^5$ and $R^6$ other than those numbered 16 or 21, with an alkanoic or arylalkanoic acid or an acylating agent derived therefrom. The acid may, for example, be acetic or benzoic acid and the acylating agent derived therefrom may be the corresponding acid chloride or anhydride. The reaction is preferably carried out in a basic solvent such as pyridine and may be accelerated or completed by heating.

j. for those compounds in which $R^1$ is a hydrogen atom, $R^2$, $R^3$, $R^4$ and $R^5$ have values other than those numbered 11, 14 or 15 and $R^6$ and $R^7$ have values other than those numbered 20 or 24, replacement by hydrogen of the cyano radical in a compound of the formula XII:

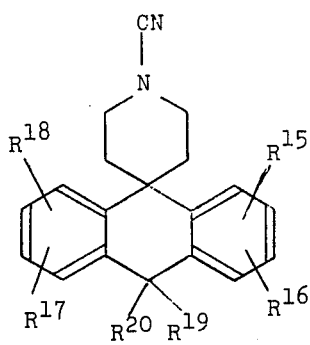

XII wherein $R^{15}$, $R^{16}$, $R^{17}$, $R^{18}$, $R^{19}$ and $R^{20}$ have the values stated above. The reaction may be carried out with a complex hydride reducing agent, for example lithium aluminium hydride, in a diluent or solvent such as diethyl ether or tetrahydrofuran. The reaction may be accelerated or completed by the application of heat, for example by heating to the boiling point of the diluent or solvent.

k. for those compounds in which $R^6$ and $R^7$ together stand for a methylene radical, dehydration of a compound of the formula XIII:

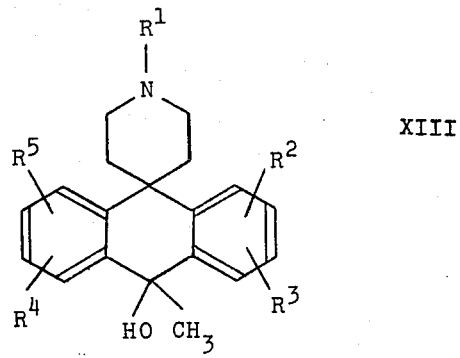

XIII

The dehydration may be accomplished with a dilute mineral acid, for example 3N HCl and the reaction may be accelerated or completed by the application of heat. or (1) for those compounds in which $R^1$ has a value other than that numbered 6 at least one of $R^2$, $R^3$, $R^4$ and $R^5$ is a hydroxy radical substituted at the 4- or 5-position and the remaining members of $R^2$, $R^3$, $R^4$ and $R^5$ have values other than those numbered 14, 15 or 16 and $R^6$ is an alkylthio radical, reaction of a compound of the formula XIV:

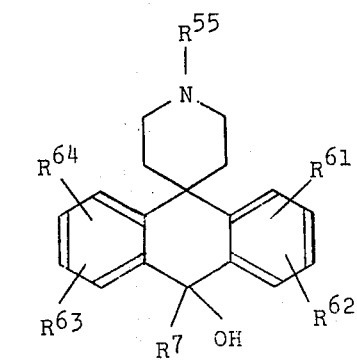

XIV wherein $R^{55}$ has the value stated above, at least one of $R^{61}$, $R^{62}$, $R^{63}$ and $R^{64}$ is a hydroxy radical substituted at the 4- or 5- position and the remaining members of $R^{61}$, $R^{62}$, $R^{63}$ and $R^{64}$ have the values stated in claim 1 for $R^2$, $R^3$, $R^4$ and $R^5$ other than those numbered 14, 15 or 16 with a compound of the formula $NaSR^{65}$ wherein $R^{65}$ is an alkyl radical. The reaction may be carried out in a diluent or solvent, for example dimethyl formamide, at an elevated temperature, for example 100°C.

The dihydroanthracene derivative of the invention may be converted into a pharmaceutically-acceptable acid-addition salt by conventional means.

The starting materials for use in the processes of the invention may be prepared, from known compounds, as described in the Examples. The following summary illustrates the general reactions involved.

The starting material of the formula III for use in process (a) may be prepared by reaction of the appropriate benzaldehyde with the appropriate bromobenzene as described in Example 10. The anion of the product, the corresponding benzhydrol, is reacted with carbon dioxide and the phthalide thus produced is reduced to the corresponding benzoic acid which is cyclised directly with polyphosphoric acid as described in Example 10 or via the derived tertiary alcohol as described in Example 1. An anthrone derivative may be prepared by reduction of the corresponding anthraquinone with copper powder in sulphuric acid as described in Example 10.

The starting material of the formula IV for use in process (b) may be prepared by dialkylation of the appropriate dihydroanthracene with allyl bromide followed by oxidation of the resulting 9,9-diallyl derivative to the corresponding diacid. This acid is cyclised to its 6-membered anhydride which is reacted with the appropriate amine to give the corresponding monoacid mono-amide which is thereafter cyclised with acetic anhydride to give the N-substituted spiro-4'-piperidin-2',6'-dione, all as described in Example 2.

The starting material of the formula VI for use in process (d) may be prepared by reduction of the appropriate 9,9-diacetic acid to the corresponding diol followed by reaction with a reagent which replaces OH with a displaceable radical, for example a halogenating agent or methanesulphonyl chloride, all as described in Example 3.

The starting material of the formula XII for use in process (j) may be prepared by reaction of the corresponding N-methyl compound wth cyanogen bromide as described in Example 14.

The replacement of chlorine by methoxy in various 9,9-diallyldihydroanthracene derivatives is described in Example 10.

The preparation of specific starting materials is described inter alia in Example 1, 2, 3, 9, 10 and 14.

The compounds of the invention have analgesic activity in warm blooded animals. This is demonstrated by activity on a number of standard tests for detecting analgesic activity, for example the mouse writhing test (Collier et al., Brit. J. Pharmac. Chemother., 1968, 32, 295; Whittle, Brit. J. Pharmac. Chemother., 1964, 22, 246) and the mouse tail clip test (Bianchi and Franceschini, Brit. J. Pharmac. Chemother., 1954, 9, 280). These tests are carried out as follows:

Tail Clip Test

10 Female mice of bodyweight approximately 20 g. each are dosed subcutaneously with the compound under test. Twenty minutes later the mice are placed in a plastic arena (30 cm. diameter) and an artery clip is placed on the tail at a distance of 1 cm. from the rump. If an individual mouse does not respond to the painful stimulus of the clip within a 10 second period, it is recorded as analgesed. In this way 50% analgesia corresponds to 5 mice in 10 showing a negative response to the clip.

Writhing Test

A painful stimulus is produced by injection of a 0.25% v/v aqueous solution of acetic acid or a 0.03% w/w aqueous solution of acetylcholine into the peritoneum of a female mouse. The characteristic response to this pain is an abdominal constriction in cojunction with a stretching of the body.

Acetic Acid Method

Of 12 20 g. female mice, 6 are dosed either subcutaneously or orally with the compound under test and the remaining 6 act as controls. Twenty minutes later all 12 mice receive an injection of the acetic acid solution (0.4 ml.) and are then placed into a plastic container divided into twelve compartments. The number of writhes of each mouse is then recorded over a 15 minute period starting 3 minutes after injection of the agent. The total number of writhes recorded for the treated group is then totalled and compared with the total found for the control group. The results are expressed as % analgesia as follows:

$$\left(100 - \frac{\text{Drug group}}{\text{Control group}} \times 100\right)$$

Acetylcholine Method

Of 12 20 g. female mice, 6 are dosed either subcutaneously or orally with the compound under test and the remaining 6 act as controls. Thirty minutes later all the 12 mice receive an intraperitoneal injection of 0.2 ml. of the acetylcholine solution and are placed on a plastic platform (30 cm. diameter). Mice which do not writhe during the minute immediately after the injection are said to be analgesed. The results are expressed as % analgesia as follows:

$$\frac{\text{No. of dosed animals not writhing}}{\text{No. of controls writhing}} \times 100$$

(On average approximately 95% of controls respond to the acetylcholine challenge).

All the compounds exemplified in this specification are active on at least one of these standard tests at a dose of equal to or less than 100 mg./kg. of the free base.

The compound of the invention 10-hydroxy-1'-methyl-9,10-dihydroanthracene-9-spiro-4'-piperidine has an oral $LD_{50}$ in mice of greater than 250 mg./kg. The corresponding intravenous $LD_{50}$ is 40 mg./kg. Other $LD_{50}$ values for compounds of the invention when dosed intravenously are as follows:

| R¹ | R² | R³,R⁴,R⁵ | R⁶ | R⁷ | LD$_{50}$ (mg./kg.) |
|---|---|---|---|---|---|
| Me | 4-OAc | H | H | H | 43 |
| Me | 2-Me | H | OH | H | 37 |
| Me | 4-OH | H | OH | Me | 25 |

Within the analgesics of the present invention at least three sub-classes can be identified.

1. Compounds in which R¹ is a methyl radical, R² has value 12, 13, 14 or 15 substituted at the 4-position, R³, R⁴ and R⁵ are hydrogen atoms and R⁶ and R⁷ have values other than that numbered 24 are narcotic analgesics, that is analgesics of the morphine type with a range of activities from codeine to morphine.

2. Compounds in which R¹ is an allyl radical, R² has value 12, 13, 14 or 15 substituted at the 4-position, R³, R⁴ and R⁵ are hydrogen atoms and R⁶ and R⁷ have values other than that numbered 24 are partial agonist analgesics, that is analgesics, of the pentazocine type, which partially antagonise the effect of morphine.

3. Compounds in which R¹ is a methyl radical, R² has value 12, 13, 14 or 15 substituted at the 4-position, R⁴ has value 9, 10, 11, 12, 13 or 14 substituted at the 5-, 6-, 7- or 8-position, R³ and R⁵ are hydrogen atoms and R⁶ and R⁷ have values other than that numbered 24 have varying mixtures of analgesic and sedative properties.

According to a further feature of the invention there is provided a pharmaceutical composition which comprises as active ingredient a dihydroanthracene derivative of the invention in association with a non-toxic pharmaceutically-acceptable diluent or carrier.

The pharmaceutical composition may be, for example, in a form suitable for oral, parenteral or rectal administration, for which purposes it may be formulated by means known to the art into the form of, for example, tablets, capsules, aqueous or oily solutions or suspensions, emulsions, sterile injectable aqueous or oily solutions or suspensions, dispersible powders or suppositories.

The pharamaceutical composition of the invention may also contain, in addition to the xanthene derivative, one or more known drugs selected from other analgesic agents, for example aspirin, paracetamol, phenacetin, codeine, pethidine and morphine, anti-inflammatory agents, for example naproxen, indomethacin and ibuprofen, neuroleptic agents such as chlorpromazine, prochlorperazine, trifluoperazine and haloperidol and other sedative drugs and tranquillisers such as chlordiazepoxide, phenobarbitone and amylobarbitone.

A preferred pharmaceutical composition of the invention is one suitable for oral administration in unit dosage form, for example tablets and capsules, which contain between 1 and 200 mg. of active ingredient, or one suitable for intravenous, intramuscular or subcutaneous injection, for example a sterile aqueous solution containing between 1 and 50 mg./ml. of active ingredient.

The pharmaceutical composition of the invention will normally be administered to man for the treatment or prevention of pain at such a dose that each patient receives an oral dose of between 30 mg. and 300 mg. of active ingredient, an intramuscular or subcutaneous dose of between 30 and 150 mg. of active ingredient or an intravenous dose of between 15 and 75 mg. of active ingredient, the composition being administered 2 or 3 times per day.

The invention is illustrated, but not limited, by the following Examples:

EXAMPLE 1

A solution of 1-methoxy-9,9-dimethyl-9,10-dihydroanthracene (2.3 g.) in dimethylsulphoxide (35 ml.) is added dropwise and with stirring to a solution of sodium methylsulphinylmethide [made in the usual way from dimethylsulphoxide (70 ml.) and sodium hydride (2 g. of a 60% dispersion in mineral oil) in an atmosphere of nitrogen]. The deep red solution is stirred for 10 minutes and N-methyl-di-(2-chloroethylamine) (2g.) in dimethylsulphoxide (50 ml.) is added dropwise, the reaction mixture is stirred for 16 hours at room temperature, and then diluted with water and extracted with ethyl acetate. The organic layer is washed with water and with brine, dried (MgSO$_4$), and evaporated to give an oil which is dissolved in the minimum volume of ethyl acetate and treated with a saturated solution of maleic acid in ethyl acetate followed by ether. The precipitated solid is recrystallised from methanol-ether to give 4-methoxy-1',10,10trimethyl-9,10-dihydroanthracene-9-spiro-4'-piperidine maleate, m.p. 193°–195°C.

The 1-methoxy-9,9-dimethyl-910-dihydroanthracene used as starting material may be prepared as follows:

To 3-methoxybenzhydrol (42.8 g.) in dry ether (800 ml.) is added 2.3 M. n-butyl lithium in hexane (250 ml.), dropwise with stirring under nitrogen. The deep red solution is stirred and heated under reflux for 2 hours and then poured into a stirred slurry of a large excess of solid carbon dioxide in ether and stirred until no carbon dioxide remains. The resulting suspension is extracted with water, the extract is acidified with concentrated hydrochloric acid, the precipitate is filtered off, washed with water, dried, and recrystallised from isopropanol to give 7-methoxy-3-phenylphthalide, m.p. 135°–138°C.

The phthalide (30 g.) is dissolved in ethanol (500 ml.) by warming, 5% palladium-on-charcoal (3 g.) is added and the solution is hydrogenated until hydrogen uptake ceases. After removal of the catalyst by filtration, the ethanol is evaporated, and the residue is crystallised from chloroform-petroleum ether (b.p. 60°–80°C.) to give 2-benzyl-6-methoxy-benzoic acid m.p. 159°–161°C.

To this acid (23 g.) in N,N-dimethylformamide (200 ml.) are added methyl iodide (30 ml.) and sodium bicarbonate (40 g.); the reaction mixture is stirred for 3 hours, diluted with a large volume of water and extracted with ether. The ether layer is washed with water, dried (MgSO$_4$), evaporated, and the residue is crystallised from ethyl acetate-petroleum ether (b.p. 60°–80°C.) to give the methyl ester of the acid m.p. 58°–59°C.

This ester (10.6 g.) in anhydrous ether (100 ml.) is added with stirring over a period of 30 minutes to methyl magnesium iodide prepared in the usual way from magnesium turnings (5 g.) and methyl iodide (30 g.). The reaction mixture is stirred and refluxed for 30 hours, poured on to ammonium chloride and ice, and extracted with ether. The ether extract is washed with brine, dried (MgSO$_4$), and evaporated to give an oil which readily crystallises. Infra-red spectroscopy shows this material to be a mixture of tertiary alcohol (~max 3450 cm$^{-1}$) and methyl ketone (~max 1690 cm$^{-1}$)

with the former predominating. Without separation the mixture is dehydrated by warming on the steam bath for 1 hour with 70% sulphuric acid (20 ml.). The suspension is added to a large volume of water and extracted with ether, the ether extract is washed with water and with brine, dried (MgSO$_4$) and evaporated to give an oil (7.6 g.) which is chromatographed on a column of silica gel (200 g.). Elution with petroleum ether (b.p. 60°–80°C.) - toluene (25:1) gives 1-methoxy-9,9-dimethyl-9,10-dihydroanthracene m.p. 62°–64°C.

The above process is repeated using an equivalent amount of 9,9-dimethyl-9,10-dihydroanthracene in place of 1-methoxy-9,9-dimethyl-9,10-dihydroanthracene as starting material and there is thus obtained 1',10,10-trimethyl-9,10-dihydroanthracene-9-spiro-4'-piperidine maleate, m.p. 222°–224°C.

EXAMPLE 2

1'-Methyl-9,10-dihydroanthracene-9-spiro-4'-piperidine-2',6',10-trione (8.7 g.) is added portionwise with stirring to lithium aluminium hydride (10 g.) in dry ether (750 ml.). The reaction mixture is heated under reflux with stirring for 40 hours and then allowed to cool, and to it is added in succession, water (10 ml.), 2N sodium hydroxide (10 ml.), and water (30 ml.), and the mixture is stirred to give a white suspension which is then filtered. The residue is washed with ether and the washings are combined with the filtrate and then evaporated to give a solid (2.28 g.). The residue from the filtration of the reaction mixture is stirred with warm chloroform and filtered, the filtrate is evaporated to give a solid (5.28 g.). The two solids are combined and recrystallised from chloroform-petroleum ether (b.p. 60°–80°C.) to give 10-hydroxy-1'-methyl-9,10-dihydroanthracene-9-spiro-4'-piperidine m.p. 208°–210°C.

The 1'-methyl-9,10-dihydroanthracene-9-spiro-4'-piperidine-2',6',10-trione used as starting material may be prepared as follows:-

10,10-Diallylanthrone (18.1 g.) in t-butanol (300 ml.) is added to sodium periodate (228 g.), potassium permanganate (3 g.), and potassium carbonate (50 g.) in water (2 l.) and the reaction mixture is stirred for 16 hours, a further 70 g. sodium periodate and 5 g. potassium permanganate are added and the reaction is stirred for a further 32 hours. It is then acidified with concentrated hydrochloric acid and extracted with ether, the ether layer is extracted with N sodium hydroxide and this extract is acidified with concentrated hydrochloric acid and extracted with ether. The ether extract is dried (Na$_2$SO$_4$) and evaporated to give crude acid which is recrystallised from aqueous methanol to give 10-oxo-9,10-dihydroanthracene-9,9-diacetic acid, m.p. 230°–2°C.

This acid (10 g.) in acetic anhydride (15 ml.) is heated under reflux for 1 hour and the solution is poured on to crushed ice and stirred until the ice has melted, the solid is filtered off, dried, and recrystallised from petroleum ether (b.p. 60°–80°C.) to give the acid anhydride m.p. 172°–173°C.

The anhydride (7.8 g.) is added to 25% aqueous methylamine (14 ml.) and the solution is allowed to stand for 20 minutes, and then poured into twice its volume of water and the mixture acidified with 2N hydrochloric acid. The precipitate is filtered off and recrystallised from aqueous methanol to give 10-oxo-9,10-dihydroanthracene-9,9-diacetic acid mono-N-methyl amide m.p. 238°–239°C.

The acid amide (2.43 g.) in acetic anhydride (10 ml.) is refluxed for 1.5 hours and then about half of the acetic anhydride is distilled off. The concentrated solution is poured on to crushed ice and when the ice has melted the resulting suspension is filtered, the solid is washed with water, dried, and recrystallised from chloroform-petroleum ether (b.p. 60°–80°C.) to give 1'-methyl-9,10-dihydroanthracene-9-spiro-4'-piperidine-2',6',10-trione m.p. 248°–249°C.

The above process is repeated using an equivalent amount of 4-methoxy-1'-methyl-9,10-dihydroanthracene-9-spiro-4'-piperidine-2',6',10-trione in place of 1'-methyl-9,10-dihydroanthracene-9-spiro-4'-piperidine-2',6',10-trione as starting material, and there is thus obtained 10-hydroxy-4-methoxy-1'-methyl-9,10-dihydroanthracene-9-spiro-4'-piperidine as the free base m.p. 149°–151°C. on recrystallisation from aqueous ethanol.

The 4-methoxy-1'-methyl-9,10-dihydroanthracene-9-spiro-4'-piperidine-2',6',10-trione used as starting material may be obtained as follows:-

1-Methoxyanthrol, isolated by following the route described in G. F. Atree & A. G. Perkin, J.Chem.Soc., 1931, 144 for the preparation of the corresponding tautomeric 1-methoxyanthrone, (15 g.) in dry tetrahydrofuran (150 ml.) is added dropwise in an atmosphere of nitrogen to a stirred suspension of sodium hydride (9 g. of a 60% dispersion in mineral oil) in dry tetrahydrofuran (250 ml.). When addition is complete, allyl bromide (42 g.) in dry tetrahydrofuran (50 ml.) is added dropwise and the reaction is stirred and heated under reflux for 3.5 hours. After the reaction mixture has been allowed to cool, water (50 ml.) is added cautiously and when effervescence ceases, more water (300 ml.) is added, the solution is acidified with concentrated hydrochloric acid, and then extracted with ether. The organic layer is washed with water and with brine, dried (MgSO$_4$), and evaporated to give a red oil. The oil is dissolved in boiling cyclohexane (300 ml.) decolourising charcoal is added, and the solution is boiled for 20 minutes, filtered, and allowed to cool whereupon 10,10-diallyl-1-methoxyanthrone m.p. 105°–107°C. crystallises.

This diallyl derivative (10 g.) in t-butanol (200 ml.) is added dropwise with vigorous stirring to potassium permanganate (1 g.), sodium periodate (123 g.) and potassium carbonate (30 g.) in water (1 l.) and the reaction mixture is stirred for 30 hours. Water (1.5 l.) is added and the solution is washed with ether, acidified with 2N-hydrochloric acid, and extracted twice with ethyl acetate and once with ether. The organic extracts are combined, washed with water and with brine and evaporated to give 4-methoxy-10-oxo-9,10-dihydroanthracene-9,9-di-acetic acid, m.p. 239°–243°C. which may be used without further purification.

From this diacetic acid are successively prepared the corresponding acid anhydride, m.p. 203°–205°C., the mono-N-methylamide, m.p. 257°–260°C. and finally 4-methoxy-1'-methyl-9,10-dihydroanthracene-9-spiro-4'-piperidine-2',6',10-trione as an oil characterised by its n.m.r. spectrum:- δ values being 3.20, 4H(s); 3.25, 3H(s); 3.98, 3H(s); 6.9–8.3, 7H(m), by the same processes described above for the preparation of 1'-methyl-9,10-dihydroanthracene-9-spiro-4'-piperidine-2',6',10-trione from 10-oxo-9,10-dihydroanthracene-9,9-diacetic acid.

EXAMPLE 3

A mixture of 9,9-di(2-methanesulphonyloxyethyl)-4-methoxy-9,10-dihydroanthracene (1.5 g.) and allylamine (7.0 g.) in n-propanol (30 ml.) is heated under reflux for 18 hours. The solvent is evaporated and 2N sodium hydroxide (20 ml.) is added; the suspension is extracted with ether and the ether layer washed with water, and extracted with 2N hydrochloric acid. The acid extract is washed with ether, basified with 15N ammonia solution, and the precipitated product is extracted into ether, the ether is washed with water and with brine, dried (MgSO$_4$) and evaporated to give 1'-allyl-4-methoxy-9,10-dihydroanthracene-9-spiro-4'-piperidine as an oil.

The 9,9-di(2-methanesulphonyloxyethyl)-4-methoxy-9,10-dihydroanthracene used as starting material may be prepared as follows:-

4-Methoxy-10-oxo-9,10-dihydroanthracene-9,9-diacetic acid, whose preparation is described in Example 2, (5.2 g.) in n-butanol (300 ml.) is heated under reflux and sodium (10 g.) is gradually added in small pieces to the boiling solution. When all the sodium has dissolved, the solution is allowed to cool and is then extracted three times with water. The aqueous extracts are combined, washed with ether and acidified with concentrated hydrochloric acid. The resulting precipitate is extracted into ether, the ether is washed with water, dried (MgSO$_4$) and evaporated to give a solid which is recrystallised from ethyl acetate-petroleum ether (b.p. 60°–80°C.) to give 4-methoxy-9,10-dihydroanthracene-9,9-diacetic acid m.p. 150°–153°C.

This diacetic acid (5.1 g.) in dry tetrahydrofuran (50 ml.) is added dropwise with stirring to lithium aluminium hydride (3.0 g.) in dry ether (250 ml.) and the reaction mixture is refluxed and stirred for 65 hours. After being allowed to cool, water (3 ml.), 2N sodium hydroxide (3 ml.) and water (9 ml.) are added in succession dropwise with stirring, ether (150 ml.) is then added and the mixture is stirred for 1 hour and filtered. The residue is washed with ether and the washings are combined with the filtrate, dried (MgSO$_4$), and evaporated to give a solid which is recrystallised from chloroform-petroleum ether (b.p. 60°–80°C.) to give 9,9-di(2-hydroxyethyl)-4-methoxy-9,10-dihydroanthracene m.p. 164°–167°C.

To a stirred solution of this diol (2.98 g.) in dry methylene chloride (100 ml.) and triethylamine (5.5 ml.) is added dropwise methanesulphonyl chloride (2.53 g.) in dry methylene chloride (20 ml.) while the reaction flask is immersed in an ice-salt cooling bath. The reaction mixture is stirred at 0°C. for 30 minutes and allowed to warm to room temperature. Chloroform (100 ml.) is added and the solution is washed twice with 2N hydrochloric acid, once with water, twice with saturated sodium bicarbonate solution, and finally with brine, then dried (MgSO$_4$) and evaporated to give an oil which crystallises and is recrystallised by addition of petroleum ether (b.p. 60°–80°C.) to a solution in the minimum volume of toluene to give 9,9-di(2-methanesulphonyloxyethyl)-4-methoxy-9,10-dihydroanthracene m.p. 128°–131°C.

The above process is repeated using the appropriate amines and substituted anthracene derivatives as starting materials, and the following compounds are obtained.

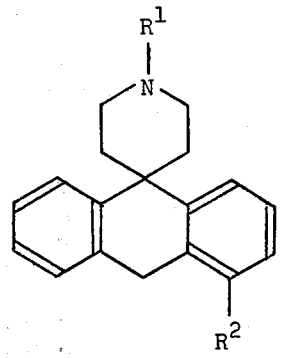

| R$^1$ | R$^2$ | Salt | M.p. (°C.) | Recrystallisation solvent |
|---|---|---|---|---|
| CH$_3$ + | OCH$_3$ | citrate | 162–165 (decomp.) | Ethanol-ether |
| (CH$_3$)$_2$CH | OCH$_3$ | oxalate | 216–218 | Methanol-ether |
| △—CH$_2$ * | OCH$_3$ | — | — | — |
| CH$_3$ + | H | free base | 132–134 | Ethanol-water |
| HCCH$_2$CH$_2$ | H | citrate | 158–161 | Ethanol-ether |
| (CH$_3$)$_2$NCH$_2$CH$_2$ | H | di-hydrochloride | 251–252 | Methanol-ether |

+prepared using 25% ethanolic methylamine in a sealed tube
* n.m.r. resonances (δvalues) at 0–1.0 cyclopropylmethyl, 2.2–2.8 piperidine ring, 3.8 0-methyl, 4.05 benzylic, 6.7–7.6 aromatic protons, in CDCl$_3$ The 9,9-di(2-methanesulphonyloxyethyl)-9,10-dihydroanthracene used as starting material may be obtained by repeating the process described above for the preparation of 9,9-di(2-methanesulphonyloxyethyl)-4-methoxy-9,10-dihydroanthracene, but using an equivalent amount of 10-oxo-9,10-dihydroanthracene-9,9-diacetic acid (whose preparation is described in Example 2) in place of 4-methoxy-10-oxo-9,10-dihydroanthracene-9,9-diacetic acid as starting material. There is thus obtained 9,10-dihydroanthracene-9,9-diacetic acid, m.p. 240°–242°C., 9,9-di(2-hydroxyethyl)-9,10-dihydroanthracene, m.p. 147°–149°C., and 9,9-di(2-methanesulphonyloxyethyl)-9,10-dihydroanthracene, m.p. 117°–119°C. respectively.

EXAMPLE 4

10-Hydroxy-1'-methyl-9,10-dihydroanthracene-9-spiro-4'-piperidine (whose preparation is described in Example 2) (1 g.) and aluminium isopropoxide (3.1 g.) are thoroughly mixed and heated to 220°C. When acetone ceases to distil off the reaction mixture is heated to 225°C. for 40 minutes and then allowed to cool. Concentrated hydrochloric acid (7 ml.) in water (10 ml.) is added and the mixture is stirred for 30 minutes, basified with 2N sodium hydroxide and extracted with ethyl acetate. The organic layer is dried (Na$_2$SO$_4$) and evaporated to give a gum which crystallises on trituration with ether and is recrystallised twice from ether-petroleum ether (b.p. 40°–60°C.) to give 1′-methyl-9,10-dihydroanthracene-9-spiro-4′-piperidine m.p. 132°–134°C.

EXAMPLE 5

To 10-hydroxy-1′-methyl-9,10-dihydroanthracene-9-spiro-4′-piperidine (whose preparation is described in Example 2) (11.5 g.) in acetone (1250 ml.) is added, dropwise with stirring, a solution of oxidising agent (32 ml.), made from sodium dichromate dihydrate (10 g.), water (30 ml.) and concentrated sulphuric acid (7.4 ml.), made up to 50 ml. with water. After addition is complete, the reaction mixture is stirred for 1 hour and is then poured into water (3 l.) basified with 2N sodium hydroxide, and extracted three times with ether. The ether extracts are combined, washed with water and with brine and evaporated to give a brown oil which is dissolved in the minimum volume of chloroform and treated with an excess of saturated ethereal citric acid. The resulting precipitate is crystallised from methanol-ether to give 1′-methyl-10-oxo-9,10-dihydroanthracene-9-spiro-4′-piperidine citrate m.p. 172°–173°C.

In a similar manner and using an equivalent amount of 10-hydroxy-4-methoxy-1′-methyl-9,10-dihydroanthracene-9-spiro-4′-piperidine (whose preparation is described in Example 2) as starting material, there is obtained 4-methoxy-1′-methyl-10-oxo-9,10-dihydroanthracene-9-spiro-4′-piperidine citrate, m.p. 170°–172°C. on recrystallisation from methanol-ether.

EXAMPLE 6

Anhydrous pyridine hydrochloride is prepared by heating pyridine (7 ml.) and concentrated hydrochloric acid (7 ml.) to 160°C. for 30 minutes. To the cooled hydrochloride is added 1′-allyl-4-methoxy-9,10-dihydroanthracene-9-spiro-4′-piperidine (1.0 g.) in ether (2 ml.) and the reaction mixture is heated to 200°C. for 30 minutes. The mixture is cooled, diluted with water, basified with solid sodium carbonate, and extracted with ethyl acetate. The ethyl acetate is washed with water and with brine, dried (MgSO$_4$), and evaporated to give a gum to which excess ethereal hydrogen chloride is added. The resultant solid is filtered off and recrystallised twice from methanol-ether to give 1′-allyl-4-hydroxy-9,10-dihydroanthracene-9-spiro-4′-piperidine hydrochloride m.p. 249°–252°C. (decomposition).

The above process is repeated using the appropriate 4-methoxydihydroanthracene derivative and the following compounds are thus obtained.

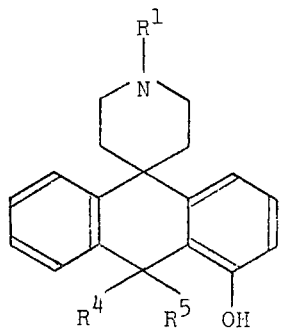

| $R^1$ | $R^4$ | $R^5$ | Salt | M.p. (°C.) | Recrystallisation solvent |
|---|---|---|---|---|---|
| CH$_3$ | CH$_3$ | CH$_3$ | maleate | 207–209 | methanol-ether |
| CH$_3$ | H | H | free base | 223–226 | methanol-water |
| CH$_3$ | 0 | | maleate | 199–201 | methanol-ether |

EXAMPLE 7

Borontribromide (2 ml.) in methylene chloride (20 ml.) is added with stirring at 0°C. to a mixture of 1′-cyclopropylmethyl-4-methoxy,9,10-dihydroanthracene-9-spiro-4′-piperidine (1.8 g.) and sodium bicarbonate (5 g.). The reaction mixture is stirred at 0°C. for 2 hours and then at room temperature for 1 hour and diluted with chloroform, more sodium bicarbonate is added, the supension is washed thoroughly with water, dried (MgSO$_4$) and evaporated. The residue is dissolved in boiling methanol, saturated ethereal hydrogen chloride is added, and the precipitated hydrochloride is collected and recrystallised twice from methanol-ether to give 1′-cyclopropylmethyl-4-hydroxy-9,10-dihydroanthracene-9-spiro-4′-piperidine hydrochloride m.p. 290°C. (decomposition).

EXAMPLE 8

4-Hydroxy-1′-methyl-9,10-dihydroanthracene-9-spiro-4′-piperidine (0.9 g.) is added to pyridine (7 ml.) and acetic anhydride (5 ml.) and the solution is warmed on the steam bath for 1 hour. It is then poured into water, basified with solid sodium carbonate, and extracted with ethyl acetate. The ethyl acetate extract is washed with water, dried (MgSO$_4$), and evaporated to give an oil to which is added an excess of a saturated solution of citric acid in ether. The resulting solid is filtered off and recrystallised three times from methanol-ether to give 4-acetoxy-1′-methyl-9,10-dihydroanthracene-9-spiro-4′-piperidine citrate m.p. 156°–159°C.

EXAMPLE 9

The process described in Example 2 is repeated using as starting material an equivalent amount of 1′,2-dimethyl-9,10-dihydroanthracene-9-spiro-4′-piperidine-2′,6′,10-trione and there is thus obtained 1′,2-dimethyl-10-hydroxy-9,10-dihydroanthracene-9-spiro-4′-piperidine, m.p. 128°–130°C. on recrystallisation from ether-petroleum ether (b.p. 40°–60°C.).

The 1′,2-dimethyl-9,10-dihydroanthracene-9-spiro-4′-piperidine-2′,6′,10-trione used as starting material may be obtained from 3-methylanthrone by repeating the processes described in the seventh, second, third, fourth and fifth parts of Example 2. There are thus obtained 10,10-diallyl-3-methylanthrone, m.p. 98–100°C. on recrystallisation from hexane, the corresponding diacetic acid, m.p. 240°C. (decomp.) on recrystallisation from acetone-chloroform, the corresponding anhydride, m.p. 199°–201°C. on recrystallisation from chloroform-petroleum ether (b.p. 60°–80°C.), the mono-N-methyl amide, m.p. 210–212°C. which is used without further purification, and 1′,2-dimethyl-9,10-dihydroanthracene-9-spiro-4′-piperidine-2′,6′,10-trione, m.p. 186°–188°C. on recrystallisation from chloroform-hexane, respectively.

EXAMPLE 10

The process described in Example 3 is repeated using the appropriate amines and substituted dihydroanthracenes as starting materials, and the following compounds are thus obtained:-

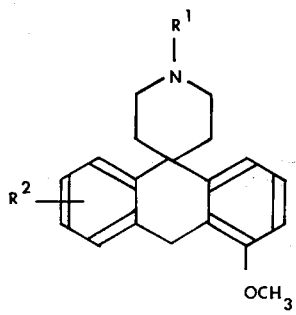

| R¹ | R² | Salt | m.p.(°C.) | Recrystallisation solvent | Foot-note |
|---|---|---|---|---|---|
| —CH₂CH₃ | H | citrate | 159–161 | ethanol-ether | 1 |
| —CH₂CH₂Ph | H | maleate | 96–98 | isopropanol-ether | 2 |
| —CH₂CH₂OH | H | free base 1 H₂O | 88–90 | ethyl acetate-petroleum ether (b.p.60–80°C.) | |
| —CH₂CH₂CH₃ | H | HCl | 204–207 | ethanol-ether | |
| —CH₂-[furyl] | H | maleate | 188–190 | ethanol-ether | |
| —CH₃ | 5-OCH₃ | maleate | 203–205 | isopropanol-petroleum ether (b.p. 30–40°C.) | 3 |
| —CH₂CH₂N(CH₃)₂ | H | HCl | 235–237 | ethanol-ether | |
| —CH₃ | 8-Cl | HCl H₂O | 209–210 | ethanol-ether | 4 |
| —CH₃ | 5-Cl | maleate H₂O | 154–156 | isopropanol-petroleum ether (b.p.30–40°C.) | 4 |
| —CH₃ | 7-CF₃ | — | — | — | 3,5 |
| —CH₃ | 6-Cl | HCl ¾ H₂O | 163–166 | ethanol-ether | 4 |

Footnotes
1 Prepared using 30% w/v ethanolic ethylamine in a sealed tube at 150°C.
2 Prepared by refluxing in xylene for 4 hours.
3 Prepared using 33% w/v ethanolic methylamine in a sealed tube at 150°C.
4 Prepared by refluxing in 33% w/v ethanolic methylamine for 18 hours.
5 Crude product used without purification in Example 12.

Starting materials for the above process may be obtained as follows:- m-Trifluoromethylbromobenzene (48 g.) in dry ether (160 ml.) is added dropwise and with stirring to magnesium turnings (5.2 g.) just covered with dry ether. After the addition of the first 10 ml. of solution, reaction is initiated by introduction of a crystal of iodine and the addition is then continued at such a rate as to maintain gentle refluxing. When all the m-trifluoromethylbromobenzene has been added and the reaction has subsided, m-methoxybenzaldehyde (27.2 g.) in dry ether (160 ml.) is added dropwise to the stirred Grignard reagent at such a rate as to maintain gentle refluxing. When all the m-methoxybenzaldehyde has been added, the reaction mixture is heated under reflux for 2 hours and then allowed to cool. Excess saturated aqueous ammonium chloride is added, the ethereal layer is separated, washed with water and with brine, dried (MgSO₄) and the ether evaporated to give an oil which crystallises and is recrystallised from petroleum ether (b.p. 40°–60°C.) to give 3-methoxy-3'-trifluoromethylbenzhydrol, m.p. 51°–52°C.

From this benzhydrol are successively prepared 7-methoxy-3-(3'-trifluoromethylphenyl)phthalide, m.p. 150°–152°C. on recrystallisation from isopropanol and 2-methoxy-6-(3'-trifluoromethylbenzyl)benzoic acid, m.p. 159°–162°C. on recrystallisation from chloroform-petroleum ether (b.p. 40°–60°C.) by repeating the processes described in the second and third parts of Example 1.

2-Methoxy-6-(3'-trifluoromethylbenzyl)benzoic acid (3.1 g.) is added in small portions with stirring to polyphosphoric acid (60 ml.) at 90°–95°C., the reaction mixture is stirred for 30 minutes at this temperature and then allowed to cool. Excess 8N ammonium hydroxide solution is added and the solution is stirred for 15 minutes and then extracted with ether. The ether layer is washed with water and with brine, and evaporated to give 1-methoxy-6-trifluoromethylanthrol, m.p. 102°–110°C., which is used without further purification.

Copper powder (1 g.) is added to 1,7-dichloroanthraquinone (1.25 g.) in concentrated sulphuric acid (10 ml.) and the mixture is stirred at 40°C. for 5 hours then poured into ice-water and extracted with ethyl acetate. The ethyl acetate extract is washed with water and with brine, dried (MgSO₄) and evaporated to give 1,7-dichloroanthrone, m.p. 160°–165°C. on recrystallisation from acetic acid.

The process used in the seventh part of Example 2 for the preparation of 10,10-diallyl-1-methoxyanthrone is repeated using the appropriate anthrones or anthrols and the following compounds are thus obtained:-

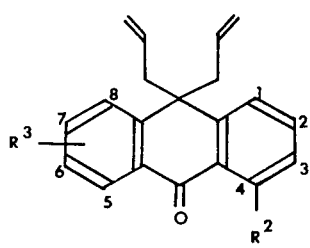

| R² | R³ | m.p.(°C.) | Recrystallisation solvent |
|---|---|---|---|
| —Cl | 5-Cl | 175–176 | isopropanol |
| —Cl | 8-cl | 137–139 | cyclohexane |
| —OCH₃ | 6-CF₃ | * | — |
| —Cl | 7-Cl | 127–130 | ** |

* n.m.r. resonances in deuterochloroform solution (δvalues) :- 2.95, 4H(d); 4.98, 3H(s); 4.75, 4H(d); 4.46–5.48, 2H(m); 6.86–8.52, 6H(m).

** Purified by chromatography on silica gel, eluting with toluene. Residue from toluene eluate triturated with petroleum ether (b.p. 60–80°C.)

Sodium (15 g.) is dissolved in dry methanol (150 ml.) and then the methanol is evaporated. Dry dioxan (300 ml.) is added to the residue and with stirring 10,10-diallyl-1,5-dichloroanthrone (15 g.) is added and the reaction mixture is refluxed and stirred for 5 hours, then allowed to cool, acidified with hydrochloric acid (3N) and extracted with ether. The ether is washed wtih water and with brine, dried (MgSO₄), evaporated, and the residue is crystallised from isopropanol to give 5-chloro-10,10-diallyl-1-methoxyanthrone, m.p. 165°–166°C.

The process described immediately above is repeated using an equivalent amount of 10,10-diallyl-1,8-dichloroanthrone and 10,10-diallyl-1,7-dichloroanthrone in place of 10,10-diallyl-1,5-dichloroanthrone and there are thus obtained 10,10-diallyl-1,8-dimethoxyanthrone, m.p. 137°–140°C. on recrystallisation from cyclohexane and 7-chloro-10,10-diallyl-1-methoxyanthrone, m.p. 130°–135°C., respectively.

In a similar process only one chloro group of 10,10-diallyl-1,8-dichloroanthrone is replaced by methoxy by conducting the reaction at room temperature and chromatographically separating the product from unchanged starting material to give 8-chloro-10,10-diallyl-1-methoxyanthrone, m.p. 151°–153°C. on recrystallisation from isopropanol.

The above 10,10-diallylanthrones are reacted as described in the second part of Example 2 to give the following dihydroanthracene acetic acids:-

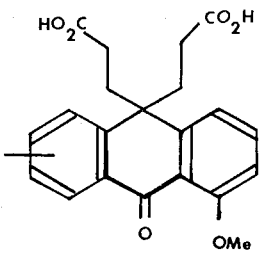

| R | m.p.(°C.) | Recrystallisation solvent |
|---|---|---|
| 5-OCH₃ | 280–285 | * |
| 5-Cl | 243–248 | * |
| 8-Cl | 296–298 | isopropanol |
| 7-CF₃ | 218–222 | * |
| 6-Cl | 212–216 | isopropanol-petroleum ether (b.p. 60–80°C.) |

*Solid prodfucts used without recrystallization.

To 4,5-dimethoxy-10-oxo-9,10-dihydroanthracene-9,9-diacetic acid (9.9 g.) in dry tetrahydrofuran (300 ml.) is added with stirring, in an atmosphere of nitrogen, diborane in tetrahydrofuran (1M, 100 ml.). The reaction mixture is refluxed for 72 hours, cooled, and water (100 ml.) is added. The tetrahydrofuran is evaporated and the remaining suspension is filtered, the residue is washed successively with aqueous sodium bicarbonate, water, a little isopropanol, and petroleum ether (b.p. 60°–80°C.) to give 9,9-di-(2-hydroxyethyl)-4,5-dimethoxy-9,10-dihydroanthracene, m.p. 193°–196°C.

The process described immediately above is repeated using the appropriate acids as starting materials, and the following compounds are thus obtained:-

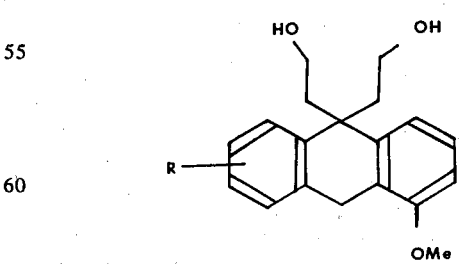

| R | m.p.(°C.) |
|---|---|
| 5-Cl | 150–155 |
| 8-Cl | 230–233 |
| 7-CF₃ | 140–145 |
| 6-Cl | 171–175 |

The process described in the fourth part of Example 3 is repeated using an equivalent amount of the appropriate diol as starting material, and the following compounds are thus obtained:-

EXAMPLE

The process described in Example 8 is repeated using the appropriate hydroxydihydroanthracene derivative as starting material and the following compounds are thus obtained:-

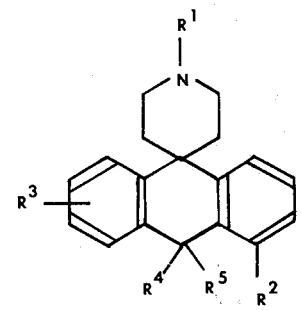

| $R^1$ | $R^2$ | $R^3$ | $R^4$ | $R^5$ | Salt | m.p. (°C.) | Recrystallisation solvent | Conditions |
|---|---|---|---|---|---|---|---|---|
| —CH$_2$CH=CH$_2$ | —OAc | H | H | H | maleate | 185–7 | methanol-ether | Room temp. 18 hr. |
| —CH$_2$CH$_3$ | —OAc | H | H | H | citrate ½ H$_2$O | 146–9 | methanol-ether | Room temp. 18 hr. |
| —CH$_2$—◁ | —OAc | H | H | H | HCl | 225–7 | isopropanol-ether | Room temp. 18 hr. |
| —CH$_2$CH$_2$CH$_3$ | —OAc | H | H | H | tartrate ½ H$_2$O | 118–120 | ethanol | Steam bath ½ hr. |
| —CH$_3$ | —H | H | —OAc | H | free base | 117–9 | chloroform-hexane | Steam bath 5 hr. |
| —CH$_3$ | —OAc | 8-Cl | H | H | maleate | 207–209 | methanol-ether | Room temp. ½ hr. |
| —CH$_3$ | —OAc | 6-Cl | H | H | HCl.H$_2$O | 159–162 | isopropanol-ether | Steam bath 1 hr. |

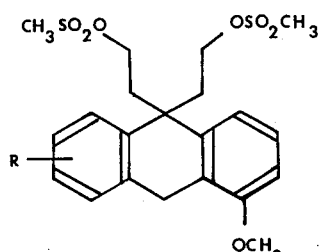

| R | m.p.(°C.) | Recrystallisation solvent |
|---|---|---|
| 5-OCH$_3$ | 171–173 | ethanol |
| 5-Cl | 165–167 | ethanol |
| 8-Cl | 121–124 | ethanol |
| 7-CF$_3$ | 117–120 | isopropanol-petroleum ether (b.p. 60–80°C.) |
| 6-Cl | 137–140 | ethanol |

EXAMPLE 12

4-Methoxy-1'-n-propyl-9,10-dihydroanthracene-9-sprio-4'-piperidine (2.5 g.) in hydrogen bromide in acetic acid (15 ml., 45% w/v) is heated under reflux for 6 hours and allowed to cool. The solution is basified with potassium carbonate and extracted with ethyl acetate, the organic layer is washed with water and with brine, dried (MgSO$_4$), and evaporated to give a solid to which is added saturated ethereal hydrogen chloride, and the resulting salt is recrystallised from methanol-ether to give 4-hydroxy-1'-n-propyl-9,10-dihydroanthracene-9-spiro-4'-piperidine hydrochloride, m.p. 285°C. (decomp.).

The above process is repeated using the appropriate methoxyspiropiperidine as starting material and the following compounds are thus obtained:-

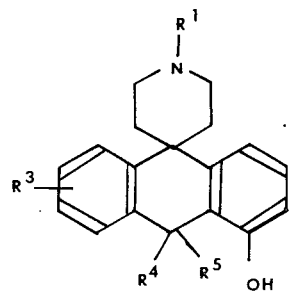

| R¹ | R³ | R⁴ | R⁵ | Salt | m.p. (°C.) | Recrystallisation solvent |
|---|---|---|---|---|---|---|
| —CH₂CH₃ | H | H | H | maleate | 206–208 | methanol-ether |
| —CH₂CH₂Ph | H | H | H | HCl ½ H₂O | 244–246 | methanol-ether |
| —CH₂CH₂N(CH₃)₂ | H | H | H | di-maleate | 139–141 | ethanol-ether |
| —CH₃ | 7-CF₃ | H | H | HCl H₂O | 137–141 | methanol-ether |
| —CH₂CH=CH₂ | H | =O | | HCl | 243–246 | ethanol-ether |
| —CH₃ | 5-OH | H | H | — | * | — |
| —CH₃ | 8-Cl | H | H | HCl ½ H₂O | 285 (decomp.) | methanol-ether |
| —CH₃ ** | 5-OCH₃ | H | H | HCl 1½ H₂O | 132–140 | isopropanol |
| —CH₃ | 6-Cl | H | H | HCl ½ H₂O | 185–187 | isopropanol-petroleum ether (b.p.60–80°C.) |

\* n.m.r. signals DMSO(d 6) (δvalues) at 1.98–2.6, 13H(m); 11H in presence of D₂O; 3.88, 2H(s); 6.63–7.15, 6H(m).
\*\* heated at 60–70°C. for 1 hour.

EXAMPLE 13

Methyl lithium in ether (5 ml., 1.5M) is added dropwise with stirring under nitrogen to 4-hydroxy-1'-methyl-10-oxo-9,10-dihydroanthracene-9-spiro-4'-piperidine (0.7 g.) in dry ether (25 ml.) and the mixture is stirred for 1 hour then diluted with water, acidified (2N hydrochloric acid), basified with sodium carbonate, and extracted with ethyl acetate. The ethyl acetate extract is washed with water and with brine, dried (MgSO₄), evaporated, and the residue is recrystallised from ethanol to give 4,10-dihydroxy-1',10-dimethyl-9,10-dihydroanthracene-9-spiro-4'-piperidine, m.p. 151°–154°C.

The above process is repeated using an equivalent amount of 1'-methyl-10-oxo-9,10-dihydroanthracene-9-spiro-4'-piperidine in place of 4-hydroxy-1'-methyl-10-oxo-9,10-dihydroanthracene-9-spiro-4'-piperidine as starting material and there is thus obtained 1',10-dimethyl-10-hydroxy-9,10-dihydroanthracene-9-spiro-4'-piperidine.1/3 H₂O, m.p. 199°–205°C. on recrystallisation from chloroform-petroleum ether (b.p. 40–60°C.).

EXAMPLE 14

1'-Cyano-4-methoxy-9,10-dihydroanthracene-9-spiro-4'-piperidine (2.3 g.) in dry tetrahydrofuran (20 ml.) is added dropwise with stirring to a solution of lithium aluminium hydride (1 g.) in dry ether (200 ml.). When addition is complete the solution is stirred and heated under reflux for 1 hour. It is then allowed to cool and water (1 ml.), sodium hydroxide solution (1 ml., 2N), water (3 ml.), and ether (100 ml.) are added in succession and the suspension is stirred for 10 minutes and then filtered. The filtrate is washed with water and with brine, dried (MgSO₄), and evaporated to give an oil which is taken up in the minimum volume of ethyl acetate and treated with a saturated solution of maleic acid in ethyl acetate. The precipitated solid is collected and recrystallised twice from isopropanol-ether to give 4-methoxy-9,10-dihydroanthracene-9-spiro-4'-piperidine maleate, m.p. 163°–165°C.

The 1'-cyano-4-methoxy-9,10-dihydroanthracene-9-spiro-4'-piperidine used as starting material in the above process may be prepared as follows:-

4-Methoxy-1'-methyl-9,10-dihydroanthracene-9-spiro-4'-piperidine (12.6 g.) and cyanogen bromide (5.6 g.) in methylene chloride (250 ml.) are stirred at room temperature for 18 hours. The reaction mixture is evaporated to dryness, and the residue is taken up in chloroform, the solution washed with water and with brine, dried (MgSO₄), and evaporated to give a brown oil which is chromatographed rapidly on silica gel. Elution with ethyl acetate affords pure 1'-cyano-4-methoxy-9,10-dihydroanthracene-9-spiro-4'-piperidine as an oil, characterised by the peak at 2200 cm⁻¹ (C N stretching) in its infra-red spectrum.

EXAMPLE 15

1'-Allyl-4-hydroxy-9,10-dihydroanthracene-9-spiro-4'-piperidine (0.2 g.) and benzoic anhydride (0.4 g.) in pyridine (2 ml.) are heated on the steam bath for 2 hours. The reaction mixture is poured into water, basified (Na₂CO₃), and extracted with ethyl acetate. The ethyl acetate extract is washed with water and with brine, dried (MgSO₄), and evaporated to give an oil which is treated with ethereal hydrogen chloride. The solid thus obtained is crystallised from isopropanol-ether to give 1'-allyl-4-benzoyloxy-9,10-dihydroanthracene-9-spiro-4'-piperidine hydrochloride, m.p. 206°–209°C.

EXAMPLE 16

1'-Allyl-4-methoxy-9,10-dihydroanthracene-9-spiro-4'-piperidine maleate (7.2 g.) in glacial acetic acid (20 ml.) is treated dropwise with stirring with chromium trioxide [60 ml. of a solution of CrO₃ (21 g.) in glacial acetic acid (190 ml.) and water (10 ml.)]. The reaction mixture is stirred for 3 hours, diluted with water, basified (NaOH), and extracted with ether. The ether extract is washed with water and with brine, dried (MgSO₄) and evaporated to give a solid which is recrystallised from cyclohexane to give 1'-allyl-4-methoxy-10-oxo-9,10-dihydroanthracene-9-spiro-4'-piperidine, m.p. 115–117°C.

In a similar manner and using an equivalent amount of 4-methoxy-1'-methyl-9,10-dihydroanthracene-9-spiro-4'-piperidine as starting material, there is obtained 4-methoxy-1'-methyl-10-oxo-9,10-dihydroanthracene-9-spiro-4'-piperidine, which forms a citrate, m.p. 170°–172°C. on recrystallisation from methanol-ether.

EXAMPLE 17

4-Methoxy-1'-methyl-10-oxo-9,10-dihydroanthracene-9-spiro-4'-piperidine (1.8 g.), in ethanol (100 ml.) is treated with sodium borohydride (2 g.), allowed to stand at room temperature overnight, then the reaction mixture is diluted with water and extracted with ether. The ether is washed with water, dried (MgSO₄) and evaporated to give an oil which is chromatographed on magnesium silicate. Elution with toluene-ethyl acetate gives 10-hydroxy-4-methoxy-1'-methyl-9,10-dihydroanthracene-9-spiro-4'-piperidine, m.p. 149°–151°C. on recrystallisation from aqueous ethanol.

EXAMPLE 18

The process described in Example 7 is repeated at −40°C. and using an equivalent amount of 5-chloro-4-methoxy-1'-methyl-9,10-dihydroanthracene-9-spiro-4'-piperidine as starting material in place of 1'-cyclopropylmethyl-4-methoxy-9,10-dihydroanthracene-9-spiro-4'-piperidine and there is thus obtained 5-chloro-4-hydroxy-9,10-dihydroanthracene-9-spiro-4'-piperidine hydrochloride hemihydrate, m.p. 191°–195°C.

EXAMPLE 19

4,10-Dihydroxy-1',10-dimethyl-9,10-dihydroanthracene-9-spiro-4'-piperidine (5 mg.) in hydrochloric acid (1 ml., 3N) is warmed on the steam bath for 10 minutes. The reaction mixture is basified with sodium carbonate and extracted with ether. The ether extract is washed with brine and evaporated to give a gum which on crystallisation from ethanol gives 4-hydroxy-1'-methyl-10-methylene-9,10-dihydroanthracene-9-spiro-4'-piperidine, m.p. 117°–120°C.

EXAMPLE 20

Sodium hydride (0.75 g. of an 80% w/w dispersion in mineral oil) is added gradually to a stirred solution of ethanethiol (1.8 ml.) in dry dimethylformamide which is cooled in an ice bath. After 20 minutes further stirring, 10-hydroxy-4-methoxy-1'-methyl-9,10-dihydroanthracene-9-spiro-4'-piperidine (1.6 g.) is added and the reaction mixture is heated at 100°C. for 3 hours, then cooled and diluted with water, acidified (2N HCl), neutralised with sodium carbonate, and extracted with ethyl acetate. The ethyl acetate extract is washed with water and with brine, dried (MgSO₄) and evaporated to give an oil which solidifies and gives 4-hydroxy-1'-methyl-10-thioethyl-9,10-dihydroanthracene-9-spiro-4'-piperidine, m.p. 117°–119°C. on recrystallisation from ethyl acetate.

What we claim is:
1. A dihydroanthrancene derivative of the formula:-

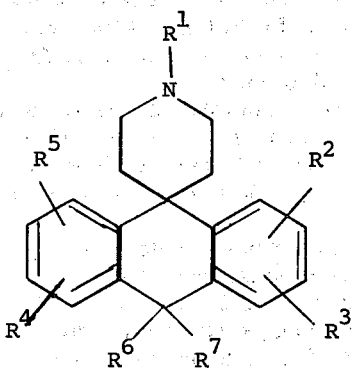

wherein
R¹ is selected from the group consisting of
1. hydrogen;
2. alkyl of 1 to 10 carbons;
3. alkenyl of 3 to 8 carbons wherein the double bond it contains is separated from the nitrogen atom of the spiropiperidine ring by at least one carbon;
4. cycloalkylalkyl of 4 to 7 carbons, optionally substituted in the cycloalkyl nucleus by an aryl of 6 to 10 carbons or by one or two alkyls of 1 to 3 carbons;
5. arylalkyl of 4 to 10 carbons, optionally substituted in the aryl nucleus by one to three halogens or alkyls of 1 to 3 carbons;
6. hydroxyalkyl of 2 to 5 carbons wherein the oxygen atom it contains is separated from the nitrogen atom of the spiropiperidine ring by at least two carbons; and
7. dialkylaminoalkyl of 4 to 8 carbons wherein the nitrogen atom it contains is separated from the nitrogen atom of the spiropiperidine ring by at least two carbons;

R², R³, R⁴ and R⁵, which may be the same or different, are selected from the group consisting of
8. hydrogen;
9. halogen;
10. alkyl of 1 to 5 carbons;
11. haloalkyl of 1 to 5 carbons;
12. alkoxy of 1 to 5 carbons;
13. hydroxy;
14. alkanoyloxy of 1 to 5 carbons;
15. aroyloxy of 7 to 10 carbons, optionally substituted in the aryl nucleus by one to three halogens or alkyls of 1 to 3 carbons; and
16. hydroxyalkyl of 1 to 5 carbons;

R⁶ is selected from the group consisting of 17. hydrogen;
18. alkyl of 1 to 3 carbons;
19. alkylthio of 1 to 3 carbons;
20. alkanoyloxy of 1 to 3 carbons; and
21. hydroxy;

and $R^7$ is selected from the group consisting of
22. hydrogen; and
23. alkyl of 1 to 3 carbons;

or $R^6$ and $R^7$ together stand for
24. oxygen or
25. methylene;

and the pharmaceutically-acceptable acid-addition salts thereof.

2. A dihydroanthracene derivative as claimed in claim 1 wherein $R^1$ stands for value 1 or 2, $R^2$ stands for value 12, 13, 14 or 15 substituted at the 4-position, $R^3$, $R^4$ and $R^5$ stand for hydrogen, $R^6$ stands for value 17, 18 or 21 and $R^7$ stands for value 22 or 23 or $R^6$ and $R^7$ together stand for methylene.

3. A dihydroanthracene derivative as claimed in claim 1 wherein $R^1$ stands for methyl, $R^2$ stands for hydroxy substituted at the 4-position, $R^3$, $R^4$ and $R^5$ stand for hydrogen, $R^6$ stands for hydroxy and $R^7$ stands for methyl.

4. A dihydroanthracene derivative as claimed in claim 1 wherein $R^2$ stands for value 8, 9, 10, 11, 12 or 16 substituted at the 2- or 3-position, $R^3$, $R^4$ and $R^5$ stand for hydrogen, $R^6$ stands for hydrogen, hydroxy or acetoxy and $R^7$ stands for hydrogen or methyl or $R^6$ and $R^7$ together stand for methylene.

5. A dihydroanthracene derivative as claimed in claim 1 wherein $R^1$ stands for methyl, $R^2$ stands for hydrogen or methyl substituted at the 2-position, $R^3$, $R^4$ and $R^5$ stand for hydrogen, $R^6$ stands for hydroxy and $R^7$ stands for hydrogen or methyl.

6. A dihydroanthracene derivative as claimed in claim 1 wherein $R^2$ stands for value 12, 13, 14 or 15 substituted at the 4-position, $R^4$ stands for value 9, 10, 11, 12, 13 or 14 substituted at the 5-, 6-, 7- or 8-position, $R^3$ and $R^5$ stand for hydrogen, $R^6$ stands for value 17, 20 or 21 and $R^7$ stands for value 22 or 23 or $R^6$ and $R^7$ together stand for oxygen.

7. A dihydroanthracene derivative as claimed in claim 1 wherein $R^1$ stands for methyl, $R^2$ stands for methoxy, hydroxy or acetoxy substituted at the 4-position, $R^4$ stands for chlorine, methyl, trifluoromethyl, methoxy, hydroxy or acetoxy substituted at the 5-, 6-, 7- or 8-position, $R^3$ and $R^5$ stand for hydrogen, $R^6$ stands for hydrogen or hydroxy and $R^7$ stands for hydrogen or methyl.

8. A dihydroanthracene derivative as claimed in claim 1 wherein $R^1$ stands for methyl, $R^2$ stands for hydroxy substituted at the 4-position, $R^4$ stands for chlorine substituted at the 6-position, and $R^3$, $R^5$, $R^6$ and $R^7$ stand for hydrogen.

9. An analgesic pharmaceutical composition which comprises as active ingredient an analgesically-effective amount of a dihydroanthracene derivative, or a non-toxic pharmaceutically-acceptable acid-addition salt thereof, claimed in claim 1, in association with a major amount of a non-toxic, pharmaceutically-acceptable diluent or carrier.

10. A method of relieving or preventing pain in warm-blooded animals including man which comprises administering an analgesically-effective amount of a compound of claim 1.

* * * * *